United States Patent [19]
Moore

[11] Patent Number: 5,627,320
[45] Date of Patent: May 6, 1997

[54] APPARATUS AND METHOD FOR AUTOMATED NON-DESTRUCTIVE INSPECTION OF INTEGRATED CIRCUIT PACKAGES

[75] Inventor: Thomas M. Moore, Dallas, Tex.

[73] Assignee: Texas Instruments Incorporated, Dallas, Tex.

[21] Appl. No.: 479,274

[22] Filed: Jun. 7, 1995

Related U.S. Application Data

[62] Division of Ser. No. 963,929, Oct. 20, 1992, which is a continuation of Ser. No. 431,686, Nov. 3, 1989, which is a continuation of Ser. No. 172,043, Mar. 23, 1988.

[51] Int. Cl.$^6$ .................................................. G01N 29/06
[52] U.S. Cl. .................................................. 73/606; 73/620
[58] Field of Search .......................... 73/606, 588, 627, 73/629, 599, 600, 620; 324/501; 364/507, 508

[56] References Cited

U.S. PATENT DOCUMENTS

| | | | |
|---|---|---|---|
| 2,633,017 | 3/1953 | Smoluchowski . | |
| 3,790,281 | 2/1974 | Kessler | 73/606 |
| 4,252,022 | 2/1981 | Hurwitz | 73/582 |
| 4,252,024 | 2/1981 | Hurwitz | 73/603 |
| 4,267,732 | 5/1981 | Quate | 73/606 |
| 4,366,713 | 1/1983 | Gilmore et al. | 73/618 |
| 4,378,699 | 4/1983 | Wickramasinghe | 73/606 |
| 4,394,824 | 7/1983 | Kanda et al. | 73/606 |
| 4,420,979 | 12/1983 | Momii et al. | 73/644 |
| 4,430,897 | 2/1984 | Quate | 73/606 |
| 4,448,525 | 5/1984 | Mikoshiba et al. | 356/73 |
| 4,484,476 | 11/1984 | Nagasaki | 73/606 |
| 4,487,069 | 12/1984 | Ishikawa et al. | 73/606 |
| 4,503,708 | 3/1985 | Kessler | 73/606 |
| 4,510,810 | 4/1985 | Kanda et al. | 73/606 |
| 4,518,992 | 5/1985 | Kessler | 73/606 |
| 4,541,281 | 9/1985 | Chubachi et al. | 73/606 |
| 4,563,900 | 1/1986 | Harada et al. | 73/644 |
| 4,567,767 | 2/1986 | Quate et al. | 73/606 |
| 4,577,504 | 3/1986 | Kanda et al. | 73/606 |
| 4,595,853 | 6/1986 | Nagatsuma et al. | 73/618 |
| 4,597,293 | 7/1986 | Kanda et al. | 73/606 |
| 4,620,443 | 11/1986 | Khuri-Yakub | 73/606 |
| 4,621,531 | 11/1986 | Nakamura et al. | 73/606 |
| 4,641,530 | 2/1987 | Attal et al. | 73/606 |
| 4,646,573 | 3/1987 | Stoll | 73/606 |
| 4,655,083 | 4/1987 | Chubachi | 73/606 |
| 4,674,333 | 6/1987 | Jindo et al. | 73/606 |
| 4,683,751 | 8/1987 | Imade et al. | 73/606 |
| 4,741,212 | 5/1988 | Rehwald | 73/606 |
| 4,751,686 | 6/1988 | Uchino et al. | 73/609 |
| 4,803,884 | 2/1989 | Kaneta et al. | 73/598 |
| 4,866,986 | 9/1989 | Cichanski | 73/600 |

*Primary Examiner*—Christine K. Oda
*Attorney, Agent, or Firm*—Stanton C. Braden; W. James Brady, III; Richard L. Donaldson

[57] ABSTRACT

A display system for non-destructive inspection of integrated circuit packages is disclosed for producing acoustical reflected images from selected planes within an integrated circuit package to detect flaws within the package.

2 Claims, 6 Drawing Sheets

APPARATUS AND METHOD FOR AUTOMATED NON-DESTRUCTIVE INSPECTION OF INTEGRATED CIRCUIT PACKAGES

This is a divisional of application Ser. No. 07/963,929, filed Oct. 20, 1992 which is a continuation of Ser. No. 07/431,686 filed Nov. 3, 1989, which is a continuation of Ser. No. 07/172,043 filed Mar. 23, 1988.

FIELD OF THE INVENTION

This invention relates to semiconductor devices and more particularly to apparatus and method of not-destructive inspection of integrated circuit packages.

DISCUSSION OF THE PRIOR ART

Innovations in ultrasonic non-destructive evaluation, or NDE, closely followed advances in electronics technology. As pulse-echo detection electronics became more sophisticated, large-scale techniques developed in the sea evolved into laboratory ultrasonic NDE devices. The field of ultrasonic NDE was launched by Floyd Firestone, a physicist at the University of Michigan. In 1942, Firestone received a patent on the "Ultrasonic Reflectoscope" which detected voids or cracks inside of manufactured parts by the pulse-echo technique using a contact transducer. Immersion methods were developed soon thereafter. The development of pulse-echo RADAR in 1938 provided the electronics capability for Firestone's Reflectoscope. Firestone's original Reflectoscope operated in the range of 2–25 MHz which provided a wavelength of 0.2–3 mm in steel.

Today's commercial NDE devices are essentially mini-SONAR systems, many of which can also produce an image, and are remarkably similar in principle to the early Reflectoscope.

In typical NDE applications, frequencies in the range of 1–5 MHz are used to penetrate highly attenuating media in search of gross flaws. Penetration is normally the dominant concern in selecting the frequency. Detection and location of a defect are usually more important than high spatial resolution imaging.

A spin-off of the ultrasonic NDE field has been medical ultrasound. In medicine, the pulse-echo technique is currently used for imaging internal organs, for determining fetal viability, and for therapeutic purposes. Medical ultrasonic imaging uses the same low frequency range as typically used for NDE applications in order to penetrate into the human body. Although only modest development has occurred in the field of NDE since the early Reflectoscope, a great deal of work has been done in improving the pulse-echo apparatus for medical ultrasonic imaging in just the last ten years. Systems using linear arrays or two dimensional phased arrays are replacing the earlier single transducer designs. This growth is no doubt stimulated by the considerable commercial opportunities for real-time medical ultrasonic imaging.

The aim of acoustic inspection of plastic-packaged IC's is the microscopic examination of internal interfaces and defects. In contrast to typical ultrasonic NDE applications, the images produced are magnified views of sub-surface interfaces. Spatial resolution at the image depth is as important as penetration, and a compromise is struck between spatial resolution and the signal/noise ratio.

Although commercial instrument manufacturers have offered images of the die-attach layer in ceramic-packaged IC's, very little work has been done in capitalizing on this capability until quite recently. In 1986, Raytheon completed a report for the Rome Air Development Center on techniques for imaging die-attach in ceramic-packaged IC's. This report recommends pulse-echo acoustic imaging above all other techniques tested including x-ray radiography and scanning laser acoustic microscopy (SLAM), due to the contrast and reliability of the pulse-echo image. The report made this recommendation in spite of the noted lack of automation available for this type of evaluation.

The die-attach layer in ceramic-packaged IC's can be imaged with higher frequencies than used for plastic package inspection due to the superior sound transmission in the ceramic material.

Hitachi has very recently release a device called the Scanning Acoustic Tomograph. This device combines a precession scanning mechanism with traditional ultrasonic NDE electronics. Only-the amplitude information is detected. Depth information is not recorded and pulse polarity information is lost due to signal rectification.

BRIEF SUMMARY OF INVENTION

The present invention is similar to the Panametrics and Hitachi pulse-echo systems, but with a novel difference. A specialized signal analysis system provides automated inspection of packaged integrated circuits. This system provides three different and important images simultaneously. One image is of the reflected amplitude of the first reflection encountered beneath the surface of the package. This image locates features of the internal structure of the integrated circuit package. The second image is a y-modulation image or color coded image of the pulse-echo response time (i.e.: depth of feature). This image is useful for plotting cracks or inclusions in the plastic above the chip or lead frame; for verifying the depth of the bar, the bar pad, and the lead fingers within the package; and for measuring curvature of the bar.

The third image highlights locations on the first internal interfaces that produce an inversion of the pulse polarity. This inversion occurs at package/void interfaces and therefore conclusively identifies delaminations at the bar surface, delaminations on the lead finger surfaces, package voids, and package cracks.

A single composite image may be generated using, for example, color coding to indicate ranges of depth and areas of polarity inversion. The amplitude image can be corrected for absorption path length differences using the depth image.

Alternately, a line scan is made across the sample and an image of distance along line scan vs. depth of reflection for all interfaces producing reflections is made (i.e.: a cross section image of the packaged part non-destructively). This is performed by on-line capturing of the transient reflection waveform, and mathematically deconvolving the reflected pulses to determine amplitude, depth, and polarity of all internal reflections. These values are used to create two cross section images with axis dimensions of line depth vs. depth. One image is of amplitude vs. depth, and one is of polarity vs. depth along the line scanned. This permits deconvolving all reflections for a true cross sectional image and not just a first or second subsurface reflection image.

Time of data reduction prevents this from being practical for imaging, although in a research environment an entire frame scan produces tomographic-like cross sections along any plane through the device non-destructively.

The technical advance represented by the invention as well as the objects thereof will become apparent from the

DESCRIPTION OF A PREFERRED EMBODIMENT

Figure 1:
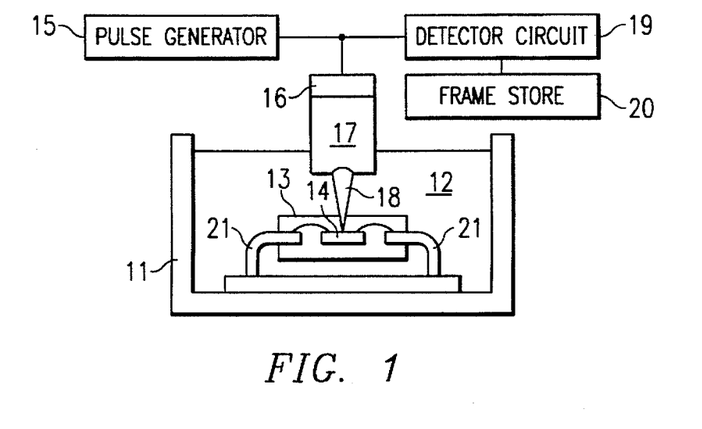
FIG. 1 illustrates apparatus for use with the present invention.

The invention uses a pulse-echo principle utilizing an apparatus such as one illustrated in FIG. 1. The system uses the acoustical reflection and is captured in an acoustic microscopy system.

The apparatus illustrated in FIG. 1 includes receptacle 11 having a coupling fluid 12 therein, for example deionized water. A semiconductor device package 13 encloses the device chip 14. The device, as illustrated may be mounted within the receptacle 11 on its own lead wires 21.

A pulse generator 15 generates and sends a pulse, for example 10 Mhz, to transducer 16. The pulse is transmitted through and focused by lens rod 17 to a sound beam as indicated by 18. This beam 18 is scanned over the surface of device 14. The echo of each pulse is reflected back to lens rod 17 through coupling fluid 12. The echo signal is transmitted from transducer 16 to detector circuit 19, and the three detected parameters are stored in frame store 20. The frame store memory is loaded synchronously with the transducer (or sample) scan index.

It is necessary to reduce the sound frequency to 30 MHz (30 Mhz is used in the prior art) before significant penetration is possible.

The shape and structure of a plastic-packaged IC are ideal for imaging with a single lens that is scanned in a two-dimensional raster over the IC. The piezoelectric transducer is extremely sensitive and the single element acoustic lens is designed, and required, to perform well only on axis. The path length through the highly attenuating package mixture is always minimized.

The pulses can be transmitted and received by a single transducer that is mechanically scanned, or with an array of transducer elements that are electronically scanned.

The absence of an irregular surface morphology on the package top surface maximizes the sensitivity to fine detail in images formed from sub-surface interface reflections. The transducer is scanned in a plane that is parallel to the planar, layered internal components in the IC package. This means that all of the internal structures lie close to the ideal focal plane. And finally, the deionized water bath and the level of insonification are considered acceptable for a non-destructive test.

For mathematical convenience it is assumed that we are dealing with the normal incidence of plane sound waves on plane interfaces, and that the materials are rigidly bonded, ideal elastic solids. Therefore, the acoustic pressure and particle velocity are considered to be continuous across an interface. The effects of well bonded, thin layers at interfaces, particularly at the bar surface, are ignored at this time because the thicknesses of these layers are much less than one acoustic wavelength in materials in the frequency range used.

Under these assumptions, there are three primary sources of information in the acoustic pulse-echo spectra recovered from a plastic-packaged IC. These are the depth of the reflection, its polarity relative to the incident pulse, and the amplitude of the reflection.

Measurements of the depth of a reflecting sub-surface interface are perhaps the most straightforward analyses that can be performed on acoustic pulse-echo spectra. This is a unique characteristic of the pulse-echo technique. A transmission technique provides information about total transmitted energy but not about the depths of interfaces in a practical method.

The depth of an interface is determined by measuring the delay between the arrival of the echo from the front surface of the package and the echo from the sub-surface interface. This time is the "round trip" time difference, or twice the time required to penetrate from the front surface to the sub-surface interface. Knowing the speed of sound in the traversed layer(s) enables one to easily calculate the depth of the sub-surface interface. In acoustic inspection of the integrated circuit, of most importance is the first sub-surface interface. In some cases the second sub-surface interface is interesting. In this case the second layer is relatively thin. In both cases, the thicknesses of the traversed layers are constant across the image plane.

The analysis of acoustic vibration is based on simple harmonic oscillation and is quite similar to classical electromagnetic radiation theory. In fact, the form of the acoustic reflectivity of an interface is similar to that for the optical reflectivity of an interface in optically transparent solids.

The optical reflectivity is based on the indices of refraction of the two layers. The acoustic reflectivity is based on the acoustic impedances of the two materials.

The characteristic acoustic impedance of layer n is given by:

$$Z_n = P_n * V_n \quad [1]$$

where $P_n$ is the density of layer n and V is the acoustic phase speed in layer n. The pressure reflection coefficient, R, is simply the ratio of the reflected pressure amplitude to the incident pressure amplitude. The form of the pressure reflection coefficient, R, follows directly from the assumptions of continuity of pressure and particle velocity across the interface:

$$R = \frac{Z_2 - Z_1}{Z_2 + Z_1} \quad [2]$$

The subscripts 1 and 2 refer to the material on the incident and on the transmitted side of the interface, respectively. When $Z_2 > Z_1$, the reflected pulse has the same polarity as the incident pulse. However, when $Z_2 < Z_1$, the reflected pulse is inverted, or has opposite polarity, with respect to the incident pulse. This polarity inversion principle will be demonstrated to be quite useful for detecting voids and delaminations in plastic-packaged IC's.

Since the reflected and incident pressure waves sum to equal the transmitted pressure wave at the interface, the pressure transmission coefficient is given by:

$$T = \frac{2 * Z_2}{Z_2 + Z_1} \quad [3]$$

Since T is always positive, the transmitted pulse is always of the same polarity as the incident pulse.

It can be seen from Equation 2 that the amplitude of the echo pulse is a function of the difference in the characteristic acoustic impedances of the materials meeting at the interface. For an ideal interface between media of identical characteristic acoustic impedance, there is no reflection. And, at the interface between media of very different characteristic acoustic impedances, there will be a strong reflection. The amplitude of the echo pulse in strongly attenuating media is also affected by the depth at which the reflection occurs.

Figure 2:
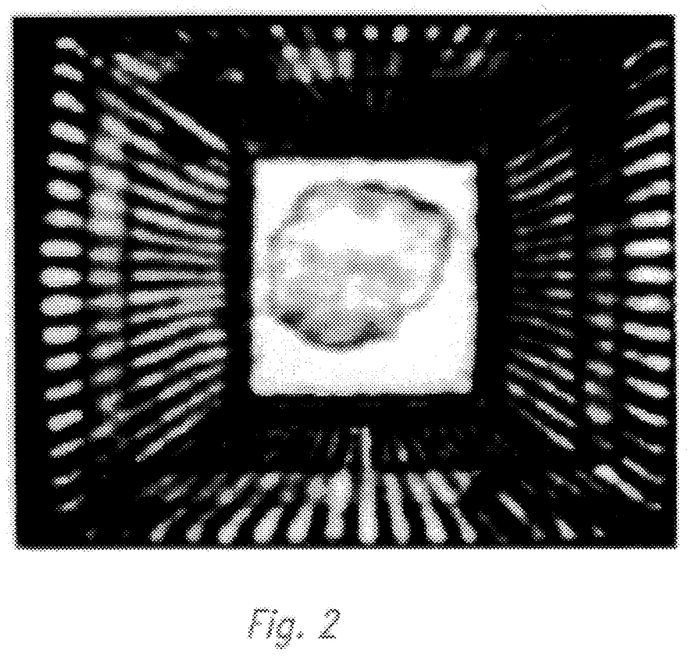
FIG. 2 is a 10 Mhz reflection acoustic image of and integrated circuit.

FIG. 2 is a 10 MHz reflection acoustic image of a 68-pin PLCC to be identified as Package A. This packaged IC has undergone one week of 85/85 (85° C., 85% rel. humidity) followed by VPR (vapor-phase reflow soldering). The expansion of trapped moisture during VPR has resulted in delamination at the package/bar interface initiating at the bar corners. The delaminated bar surface areas appear brighter in FIG. 2.

This type of failure seriously affects the reliability of the gold wire bonding and the dissipation of heat from the bar.

Figure 3:
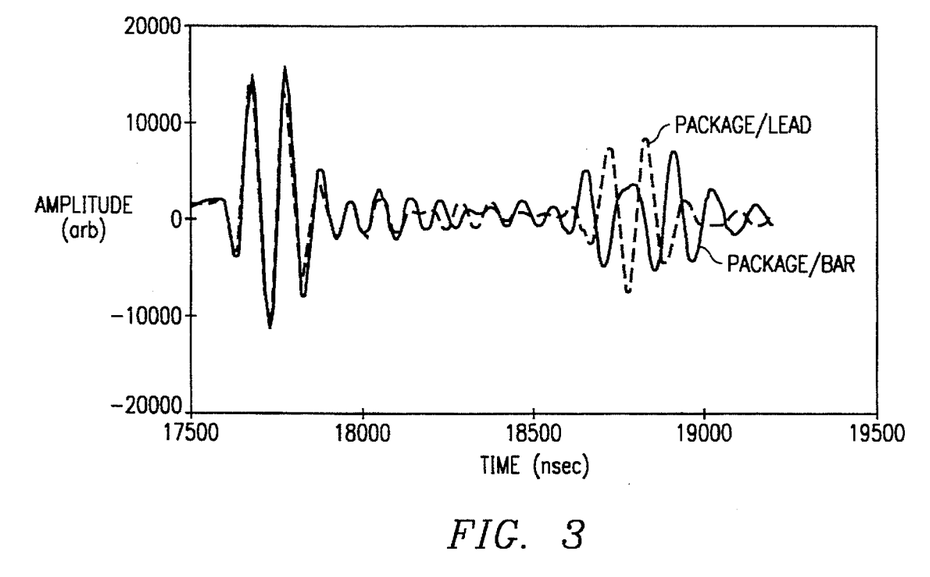
FIGS. 3 and 4 are portions between 17500 and 19500 ns of typical acoustic reflection spectra form different points on an integrated circuit package.
Figure 4:
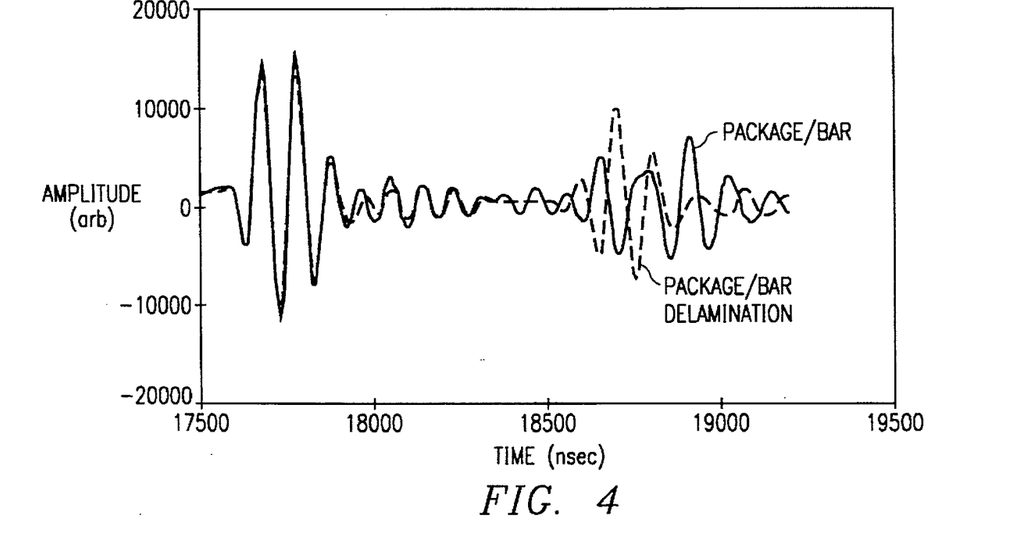

FIGS. 3 and 4 are the portions between 17500 and 19500 ns of typical acoustic reflection spectra from different points on Package A. FIG. 3 shows the echo spectra of the reflections from the package/bar interface at the center of the bar. The package/lead interface in Package A overlaid for comparison. FIG. 4 shows the echo spectra for the package/bar interface at locations of good adhesion and of delamination overlaid for comparison.

The reflected pulse at 17500 to 18000 ns that is essentially common to all these spectra is from the package surface. Since the acoustic impedance of water is less than that of the package material, the package surface reflection must be of the same polarity as that of the incident pulse.

The acoustic impedance of the package material is less than that of silicon or of the metal lead frame material, so both the package/lead and the package/bar interface reflections in FIG. 3 are of the same polarity as the package surface reflection, and therefore of the same polarity as the pulse incident on the package surface.

Figure 5:
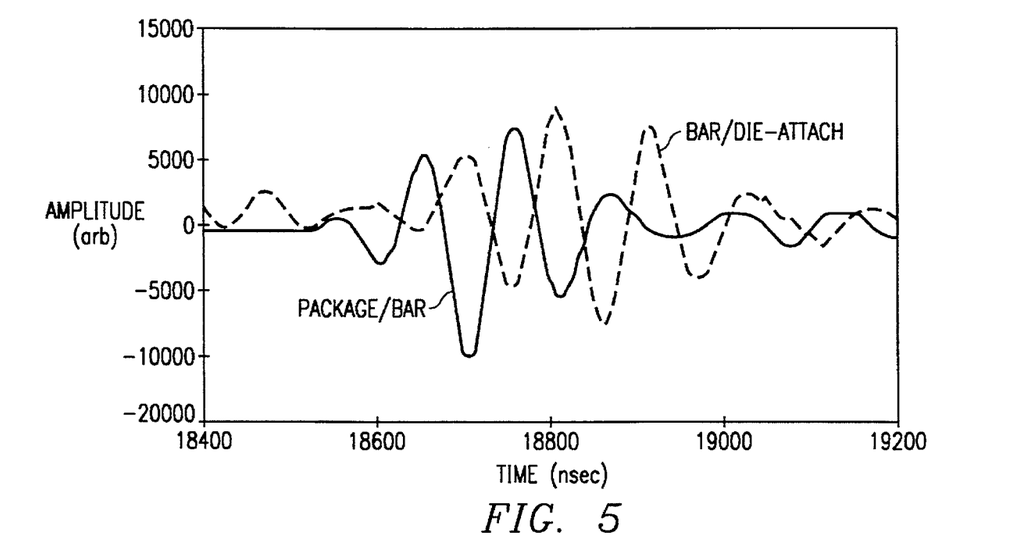
FIG. 5 is a deconvolution of the two reflections shown in FIG. 3.

The package/bar reflection in FIG. 3 is taken over the center of the bar in Package A where the package remains adhered to the bar surface. This is the same spectrum as that overlaid with the spectrum of a package/bar delamination shown in FIG. 4. Note that the package/bar interface reflection in FIG. 3 is actually two reflections superposed. FIG. 5 is a deconvolution of these two reflections shown on an expanded time base. The second reflection is delayed due to the penetration through approximately 450 um of silicon twice and is from the bar/die-attach interface. A unique lobe on this second, or die-attach pulse is used to image voiding in the die-attach layer.

The characteristic acoustic impedance of a void, or of package material that has penetrated under the bar into a die-attach void, will also be less than that of silicon. The characteristic acoustic impedance of a void will is assumed to be that of air. Therefore, delamination at the bar/die-attach interface will not be distinguishable by localized phase inversion.

Figure 6:
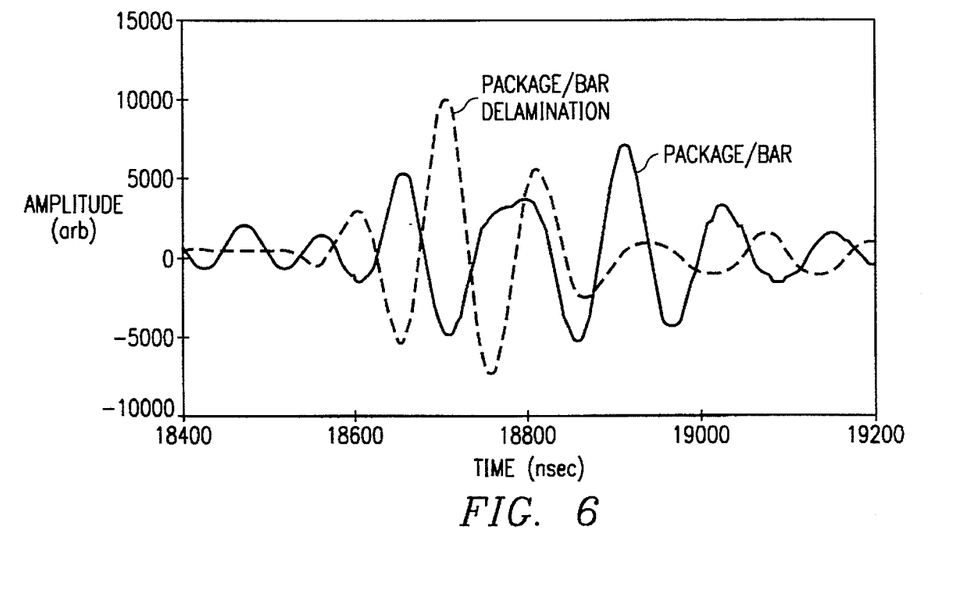
FIG. 6 is an expanded time base view of FIG. 5.

FIG. 6 is an expanded time base view of FIG. 4 showing two typical reflections from the package/bar interface in Package A. Note that the reflection from the delaminated interface is of opposite polarity relative to that from the location showing adhesion.

This is due to the fact that the void has a lesser characteristic acoustic impedance than does package material. And, as noted earlier, silicon has a greater characteristic acoustic impedance than does package material. Therefore, at the package/bar interface, the reflection from the location showing good adhesion has the same polarity as the pulse incident on the package surface, while the reflection from a delaminated location will have opposite polarity. Also, the reflection from the delaminated location is a single pulse since the die-attach interface at his location is in the shadow of the delamination, acoustically speaking.

Since the acoustic impedance mismatch is greater at the delaminated location, under ideal focusing conditions, this reflection has a greater amplitude than that from the location showing adhesion. Therefore, locations of delamination at the package/bar interface may be distinguished by a locally greater reflected amplitude, under ideal conditions, and are always distinguished by a locally inverted pulse polarity. However, delaminations at the package/lead interface are not conclusively distinguishable by reflected pulse amplitude, and pulse polarity detection is critical for imaging these areas.

Figure 7:
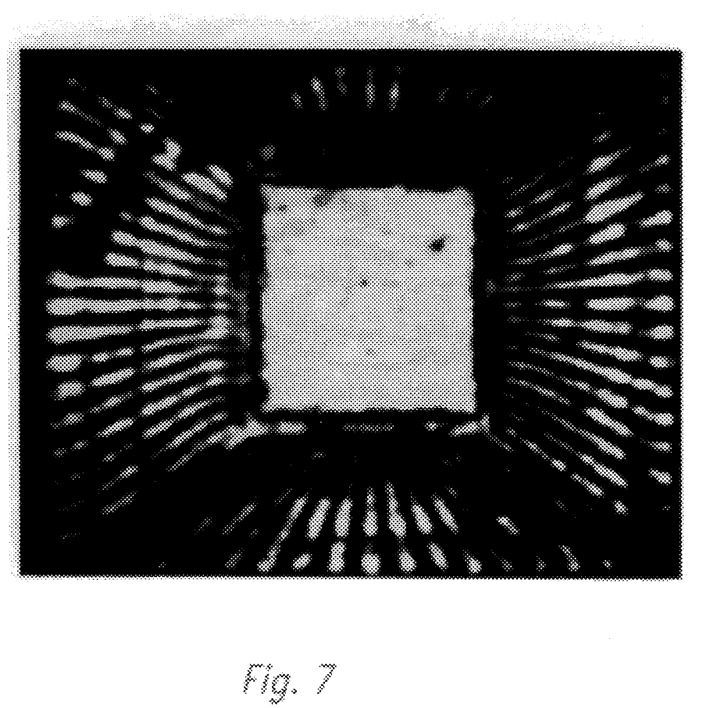
FIG. 7 is a 10 Mhz reflection acoustic micrograph of a second integrated circuit.

FIG. 7 is a 10 MHz reflection acoustic micrograph of another 68-pin PLCC identified as Package B. Package B was exposed to one week of 85/85 followed by the solder dip process. The entire package/bar interface is delaminated, as revealed by pulse polarity analysis.

Figure 8:
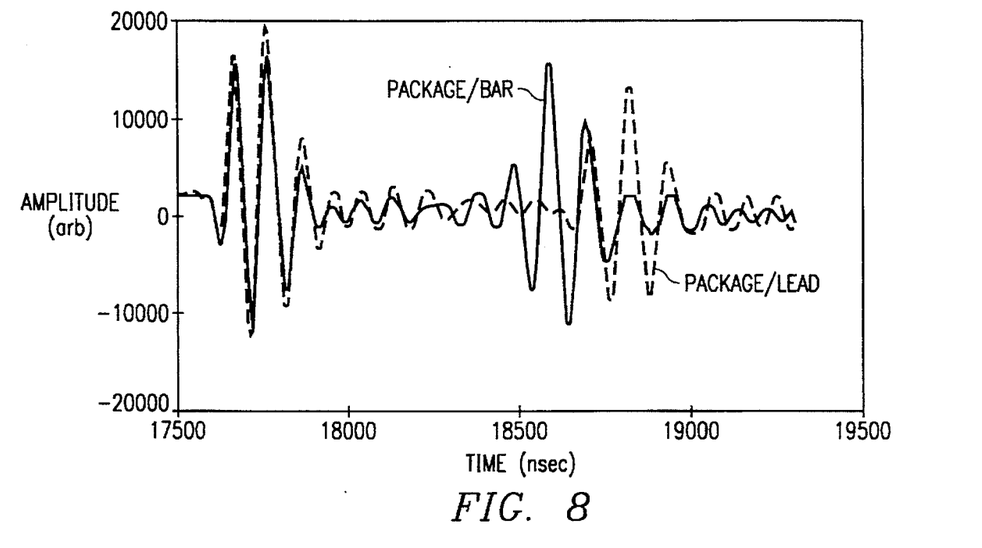
FIG. 8 shows the acoustic reflection spectra for the package/bar and package/lead interfaces of the second integrated circuit of FIG. 7.

FIG. 8 shows the acoustic reflection spectra for the package/bar and package/lead interfaces. Note that the package/bar reflection has inverted polarity relative to the pulse incident on the package surface. Also, note that the bar pad is significantly higher in the package compared to Package A.

There are two distinct acoustic shadows in FIG. 7 in the upper left corner of Package B. A time window enclosing the package/bar and package/lead interfaces was used to form the image in FIG. 7. The acoustic shadows are formed by cracks in the package above the package/bar interface. Reflections from these cracks are therefore not included in the image in FIG. 7. Since these cracks exhibit total reflection, all interfaces below them are acoustically shadowed. So the cracks are revealed in FIG. 7 by the acoustic shadows they create. The present invention will image such cracks and identify them by their depth and profile.

Figure 9:
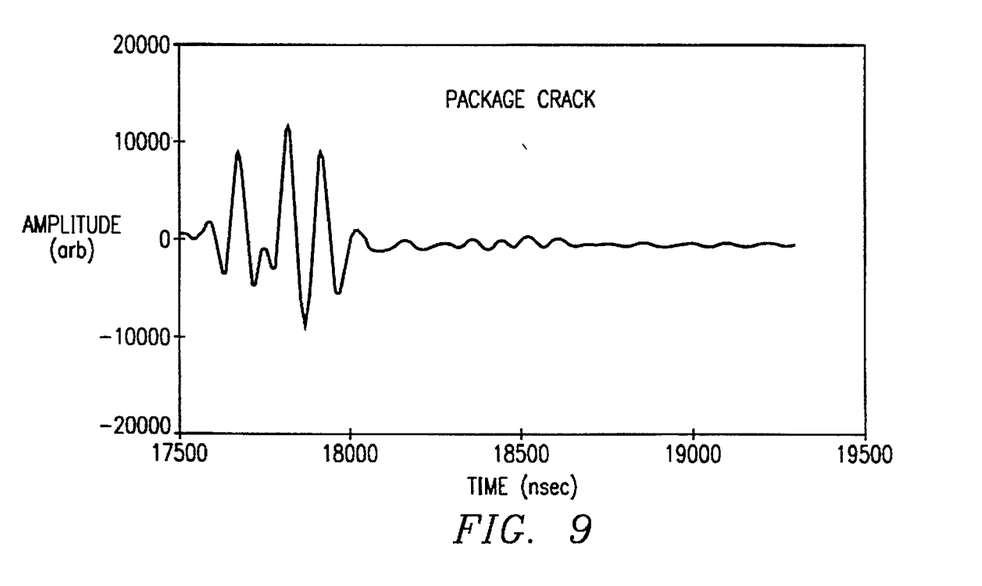
FIG. 9 is an acoustic spectrum of a crack in the package of FIG. 7.

An acoustic spectrum at the location of one of these cracks is shown in FIG. 9. The reflection from the crack partially interferes with the package surface reflection and no later reflections are detected.

Figure 10:
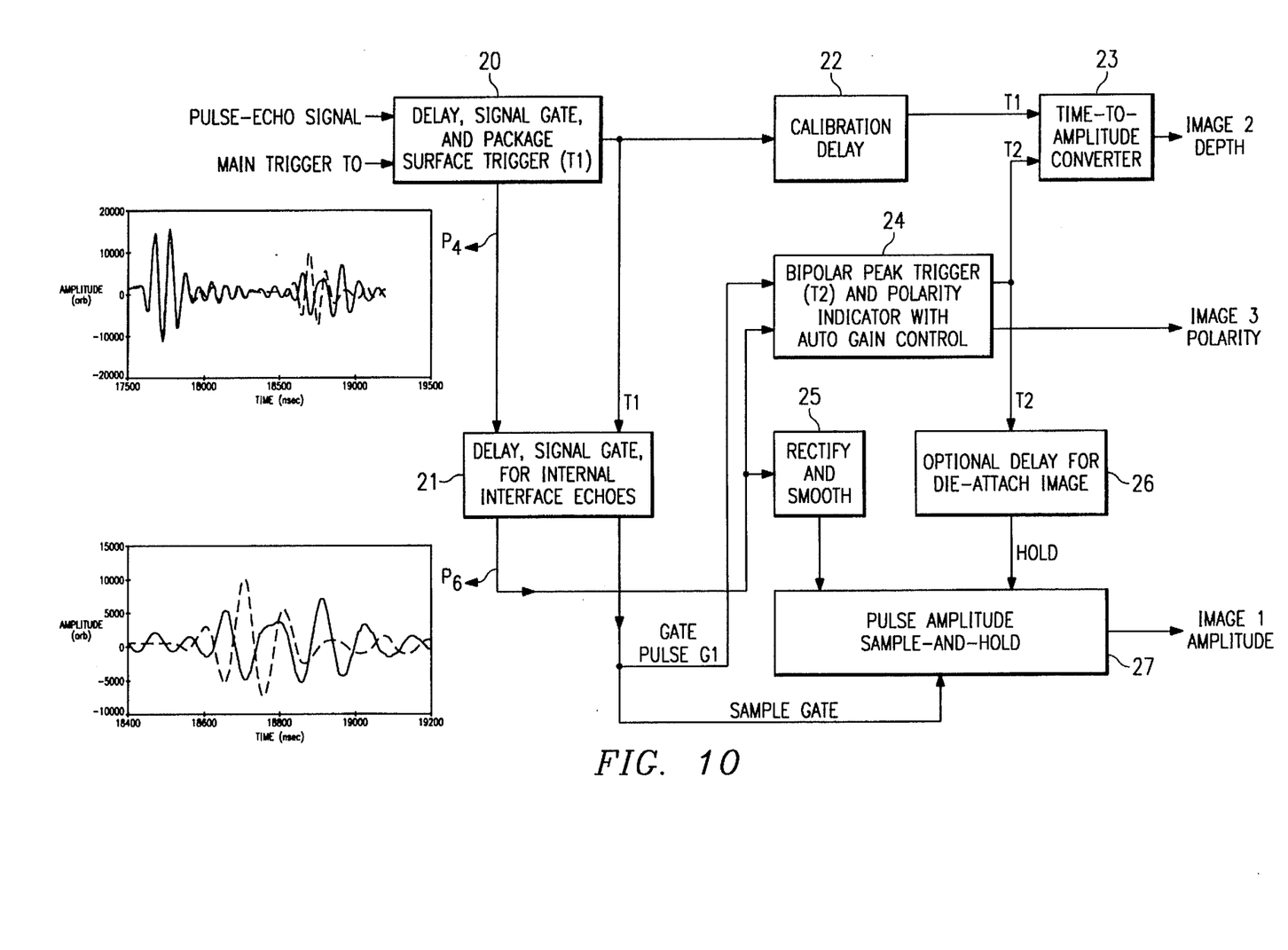
FIG. 10 is a block diagram of the detector circuit.

FIG. 10 is a block diagram of the detector circuit used in the present invention. The pulse-echo signal is gated in time using the main trigger ($T_0$), and a time delay, to indicate only the package surface reflection.

Threshold trigger circuit 20 detects the integrated circuit package surface reflection and generates a timing trigger $T_1$. The pulse echo signal is gated again (in gate 21) using $T_1$, using a time delay to indicate only the reflections from inside the integrated circuit package. The delayed pulse-echo signal present at point $P_4$ is illustrated in FIG. 4.

A gate pulse $G_1$ is generated in gate 21 to indicate the occurrence and duration of the gate spectrum of the reflections inside the package. The spectrum of reflections from inside the integrated circuit package is output from gate 21 and is present at point $P_6$. The spectrum of reflections present at point $P_6$ is illustrated in FIG. 6.

The spectrum of reflections form inside the integrated circuit package is passed into the bipolar peak detector 24 which generates a timing trigger $T_2$ when a peak above a set threshold is detected. The bipolar peak detector 24 is enabled by the gate pulse $G_1$ from gate circuit 21.

The bipolar peak detector circuit 24 also generates an indication of the polarity of the first internal reflection by sensing the polarity of the first major positive lobe in either the inverted or non-inverted pulse. An automatic gain control amplifier and threshold trigger (in block 24) or a constant fraction discriminator, or similar circuit is used as a lobe detector. This polarity indication, for example: a D.C. level output of +5 V for inverted and 0 V for normal, is used to form the polarity image.

The spectrum of reflections from inside the integrated circuit is also rectified and smoothed (block 25) to provide a pulse that is always positive for amplitude detection.

A sample-and-hold circuit 27 is used to capture a representative amplitude, from the rectify and smooth circuit 25, for the first internal reflection. Trigger $T_2$ is used to hold the amplitude level and the gate pulse $G_1$ from the second signal gate 21 is used to enable the sample-and-hold amplifier. This representative amplitude is used to form the amplitude image. There is an optional delay circuit 26 which may be used to delay trigger $T_2$ before it is applied to the sample-and-hold circuit 27.

Trigger $T_1$, from delay-signal gate 20 is delayed by calibration delay 22 to compensate for the artificial delay added to trigger $T_2$ by delay-signal gate 21 and the bipolar peak trigger circuit 24, and the delay of trigger $T_1$ is calibrated.

The delayed trigger $T_1$ and trigger $T_2$ are input into a time-to-amplitude converter 23. A DC level is generated which corresponds to the delay between the triggers, and therefore corresponds to the depth of the first internal interface. The output of the Time-to-Amplitude circuit 23 is used to form the depth image.

Each of the three images, Amplitude, Depth, and Polarity is stored in separate frame store memory (not illustrated), and the location of each image within each frame store is scanned synchronously with the location of the scanned transducer.

What is claimed is:

1. A display system for a scanning acoustic microscope having a transducer system operable to generate a series of acoustic pulses of ultrasonic frequency and predetermined magnitude, an acoustic scanning system operable to direct the acoustic pulses to impinge upon and insonify an object with predetermined timing and in accordance with a preselected scanning pattern, and a receiver system operable to receive ultrasonic pulse echoes reflected from the object and to develop an initial electrical signal of varying amplitude and polarity representative of the magnitude and phase, respectively, of the ultrasonic pulse echoes, the display system comprising:

a) a signal amplifier connected to the receiver system and operable to generate an amplitude content signal representative of amplitude of the initial electrical signal, independent of polarity;

b) a signal comparator connected to the receiver system and operable to generate a polarity content signal representative of polarity of the initial electrical signal, independent of amplitude; and c) a signal display actuated by the respective amplitude and polarity content signals, operable to display a unified, consolidated image of the object in which acoustic impedance transitions for at least one depth level of the object from which echoes of different polarities occur are distinguished from each other.

2. A display system for a scanning acoustic microscope having a transducer system operable to generate a series of acoustic pulses of ultrasonic frequency and predetermined magnitude, an acoustic scanning system operable to direct the acoustic pulses to impinge upon and insonify an object with predetermined timing and in accordance with a preselected scanning pattern, and a receiver system operable to receive ultrasonic pulse echoes reflected from the object and to develop an initial electrical signal of varying amplitude and polarity representative of the magnitude and phase, respectively, of the ultrasonic pulse echoes, the display system comprising:

a) a signal amplifier connected to the receiver system and operable to generate an amplitude content signal representative of amplitude of the initial electrical signal, independent of polarity;

b) a signal comparator connected to the receiver system and operable to generate a polarity content signal representative of polarity of the initial electrical signal, independent of amplitude; and c) a discrete storage register for each of said amplitude and polarity content signals; and d) a signal display, actuated by the respective amplitude and polarity content signals stored in the respective registers operable to display a unified, consolidated image of the object in which acoustic impedance transitions for at least one depth level of the object from which echoes of different polarities occur are distinguished from each other.

\* \* \* \* \*